United States Patent [19]

Simons et al.

[11] 4,255,510

[45] Mar. 10, 1981

[54] DEVELOPMENT RESTRAINER PRECURSORS FOR PHOTOGRAPHIC ELEMENTS

[75] Inventors: Michael J. Simons, Eastcote; David T. Southby, West Harrow, both of England; Hans G. Ling, Rochester, N.Y.

[73] Assignee: Eastman Kodak Company, Rochester, N.Y.

[21] Appl. No.: 85,944

[22] Filed: Oct. 18, 1979

[30] Foreign Application Priority Data

Oct. 20, 1978 [GB] United Kingdom ............ 41437/78

[51] Int. Cl.³ .................. G03C 1/40; G03C 7/00; G03C 1/10; G03C 5/30
[52] U.S. Cl. ..................... 430/219; 430/240; 430/382; 430/390; 430/446; 430/486; 430/544; 430/559; 430/613; 430/957
[58] Field of Search .......... 430/219, 240, 382, 390, 430/446, 486, 489, 544, 559, 613, 957

[56] References Cited

U.S. PATENT DOCUMENTS

| | | | |
|---|---|---|---|
| 3,260,597 | 7/1966 | Weyerts et al. | 430/219 |
| 3,265,498 | 8/1966 | Rogers et al. | 430/219 |
| 3,364,028 | 1/1968 | Konig | 430/613 |
| 3,575,699 | 4/1971 | Bloom et al. | 430/446 |
| 3,649,267 | 3/1972 | Carlson | 430/219 |
| 3,856,520 | 12/1974 | Bloom et al. | 430/219 |
| 3,893,859 | 7/1975 | Borness et al. | 430/613 |
| 4,076,529 | 2/1978 | Fleckenstein et al. | 430/223 |

FOREIGN PATENT DOCUMENTS

2282124 4/1975 France.

OTHER PUBLICATIONS

"Blocked Development Restrainers", *Research Disclosure* No. 13118, 3/1975 pp. 31-36.

*Primary Examiner*—Richard L. Schilling
*Attorney, Agent, or Firm*—Harold E. Cole

[57] ABSTRACT

Photographic elements, assemblages and processes for color diffusion transfer photography are described wherein certain azole compounds having at least two nitrogen atoms are employed as development restrainer precursors. Preferred azole compounds include benzotriazoles, triazoles, tetrazoles, indazoles and benzimidazoles. The azole compounds have an alkali-hydrolyzable, N,N-disubstituted carbamoyl group on one of the two nitrogen atoms.

33 Claims, No Drawings

DEVELOPMENT RESTRAINER PRECURSORS FOR PHOTOGRAPHIC ELEMENTS

This invention relates to photography, and more particularly to photographic elements and assemblages for color diffusion transfer photography wherein certain azole compounds having an alkali-hydrolyzable, N,N-disubstituted carbamoyl group are employed as development restrainer precursors.

U.S. Pat. No. 4,076,529 of Fleckenstein et al, issued Feb. 28, 1978, describes various color image transfer elements which employ nondiffusible, redox dye-releasing compounds which are alkali-cleavable upon oxidation to release a diffusible color-providing moiety. Development restrainers or precursors thereof are usually employed in such elements to try to progressively slow down the rate of development during the latter stages of the process without adversely affecting the initial development rate.

Various blocked antifoggants and development restrainers are disclosed in Japanese Patent No. 586,882 and U.S. Pat. Nos. 3,364,028, 3,575,699 and 3,649,267. These references do not disclose the compounds useful in our invention, however.

*Research Disclosure* article 13118, March 1975, discloses various blocked benzotriazoles useful as development restrainers in color diffusion transfer elements. Such compounds have been found to become hydrolyzed by the alkaline processing composition too rapidly, however. In some instances, hydrolysis is essentially complete in ten seconds or less. When that happens, the initial development rate is adversely affected.

The compounds employed in our invention hydrolyze at a much slower rate than those of the prior art. In a 0.1 M aqueous sodium hydroxide solution, our compounds typically have a half-life of ten seconds to several minutes. These compounds have the desired property of progressively restraining development without adversely affecting the initial development rate.

A photographic element in accordance with our invention comprises a support having thereon at least one photosensitive silver halide emulsion layer having associated therewith a dye image-providing material, and wherein the element contains an azole compound comprising an azole ring having at least two nitrogen atoms, said compound having an alkali-hydrolyzable, N,N-disubstituted carbamoyl group on one of the two nitrogen atoms.

In a preferred embodiment of our invention, the azole compound which is employed has the following formula:

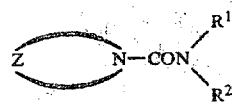

wherein:
R$^1$ and R$^2$ each represent a substituted or unsubstituted alicyclic, aliphatic, aromatic or heterocyclic moiety, or may be taken together with the nitrogen to which they are attached to form a heterocyclic ring; and Z represents the atoms necessary to complete an azole ring containing at least two nitrogen atoms.

In the above formula, R$^1$ and R$^2$ can each be a substituted or unsubstituted alicyclic group, such as cycloalkyl of 3 to 20 carbon atoms; e.g., cyclopropyl, cyclohexyl, cyclodecyl or cyclooctadecyl; an aliphatic group, such as a straight or branched chain alkyl group of 1 to 20 carbon atoms, including aralkyl and aryloxyalkyl, e.g., methyl, ethyl, isopropyl, butyl, hydroxyethyl, octyl, pentyl, dodecyl, pentadecyl, octadecyl, benzyl, furfuryl, or phenoxypropyl; an aromatic group, such as aryl of 6 to 20 carbon atoms, including alkaryl and alkoxyaryl, e.g., phenyl, naphthyl, methylphenyl, 4-methoxyphenyl, p-sulfamoylphenyl, p-dodecylphenyl, butoxyphenyl; or a heterocyclic moiety containing from 5 to 20 nonmetallic atoms, such as thienyl, pyridyl, or pyrimidyl; or may be taken together with the nitrogen to which they are attached to form a heterocyclic ring, such as morpholine, piperidine, pyrrolidine, piperazine, etc. In a preferred embodiment of the invention, each R$^1$ and R$^2$ is a substituted or unsubstituted alkyl or aryl group, as described above. In a more preferred embodiment, each R$^1$ and R$^2$ is ethyl, phenyl, 4-methoxy-phenyl or —(CH$_2$)$_{10}$—COOC$_2$H$_5$, or are taken together to complete a morpholine or piperidine ring.

As stated above, Z represents the atoms necessary to complete an azole ring containing at least two nitrogen atoms. In a preferred embodiment of the invention, Z represents the atoms necessary to complete a benzotriazole, triazole, tetrazole, indazole or benzimidazole ring. Such rings may be substituted with lower alkyl groups, halogen atoms, nitro groups, etc.

In another preferred embodiment of the invention, Z represents the atoms necessary to complete a benzotriazole ring. In a more preferred embodiment, the benzotriazole compound can have either of the following formulas:

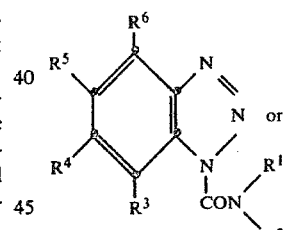

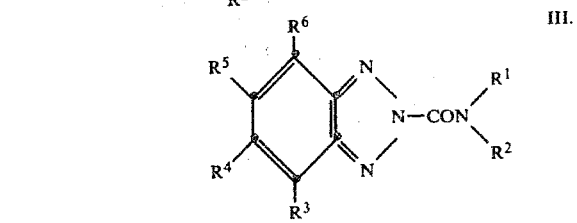

wherein:
R$^1$ and R$^2$ are as defined above; and
R$^3$, R$^4$, R$^5$ and R$^6$ each represent hydrogen, nitro, lower alkyl (including substituted alkyl) of 1 to 6 carbon atoms, such as methyl, ethyl, propyl, isopropyl, hexyl, carboxymethyl, etc; halogen, such as chloro, bromo, etc; carbamoyl, sulfamoyl, RCONH— or RSO$_2$NH—, wherein R is a lower alkyl group of 1 to 6 carbon atoms, such as methyl, ethyl, propyl, isopropyl, hexyl, carboxymethyl, etc, or an aryl group of 6 to 10 carbon atoms, such as phenyl, tolyl, etc.

Typical compounds included within the scope of the above formula include the following:
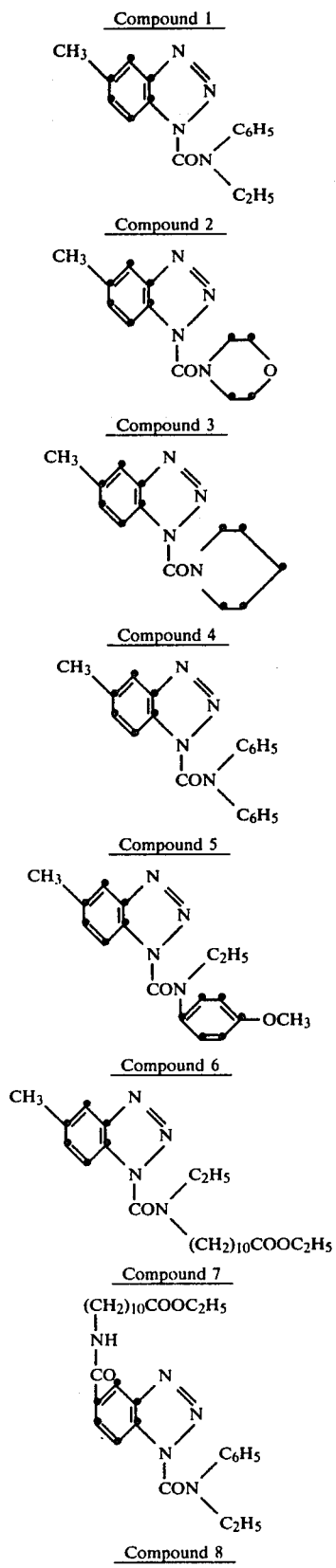
Compound 1
Compound 2
Compound 3
Compound 4
Compound 5
Compound 6
Compound 7
Compound 8
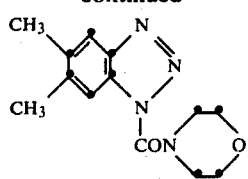
Compound 9
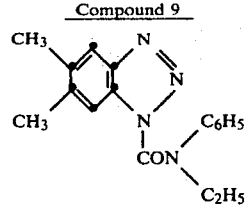
Compound 10
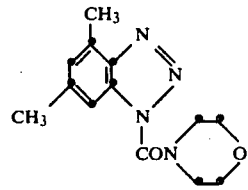
Compound 11
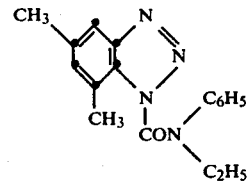
Compound 12
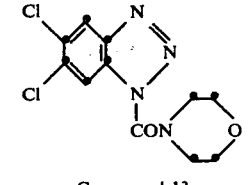
Compound 13
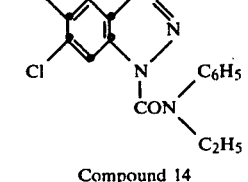
Compound 14
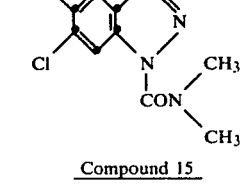
Compound 15
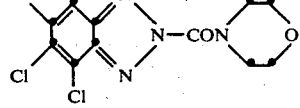
Compound 16

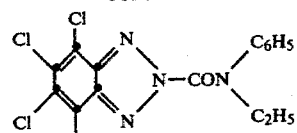
Compound 17

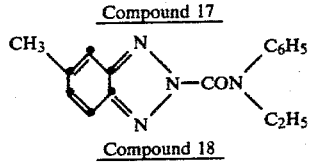
Compound 18

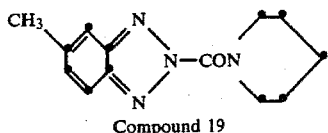
Compound 19

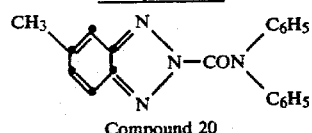
Compound 20

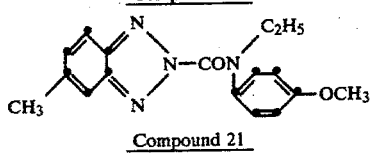
Compound 21

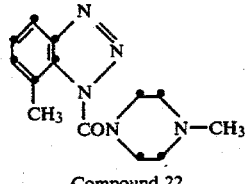
Compound 22

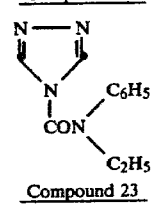
Compound 23

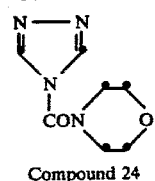
Compound 24

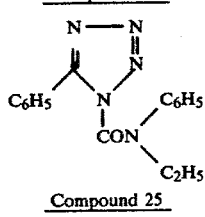
Compound 25

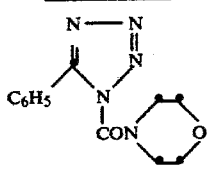
Compound 26

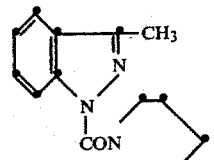
Compound 27

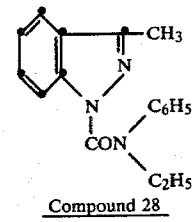
Compound 28

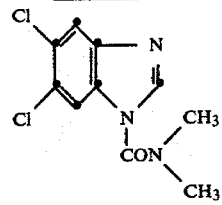
Compound 29

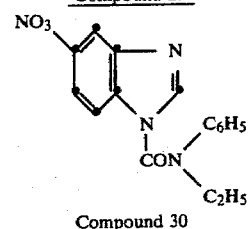
Compound 30

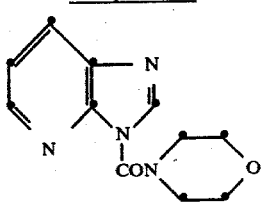
Compound 31

The development restrainer precursors employed in this invention may be incorporated into any layer of the photographic element described above. They may be incorporated into the silver halide emulsion layer, the dye image-providing material layer, interlayers, etc. They may be employed in any amount suitable for the intended purpose. In general, good results are obtained when the compounds are employed in a concentration range of from 0.05 to 1.5 grams per square meter of element. The compounds may be incorporated as solutions, as fine particulate dispersions, or dissolved in droplets of a high-boiling solvent.

The dye image-providing material useful in our invention can be positive- or negative-working, and can be initially mobile or immobile in the photographic element during processing with an alkaline composition. Examples of initially mobile, positive-working dye image-providing materials useful in our invention are described in U.S. Pat. Nos. 2,983,606; 3,536,739; 3,705,184; 3,482,972; 2,756,142; 3,880,658 and 3,854,985. Examples of negative-working dye image-providing materials useful in our invention include conventional couplers which react with oxidized aromatic primary amino color developing agents to produce or release a dye such as those described, for example, in U.S. Pat. No. 3,227,550 and Canadian Patent No. 602,607. In a preferred embodiment of our invention, the dye image-providing material is a ballasted, redox-dye-releasing (RDR) compound. Such compounds are well known to those skilled in the art and are, generally speaking, compounds which will redox with oxidized developing agent or electron transfer agent to release a dye, such as by alkaline hydrolysis, or prevent the release of dye, such as by intramolecular nucleophilic displacement. Such nondiffusible RDR's can be positive-working compounds, as described in U.S. Pat. No. 3,980,479, British Pat. No. 1,464,104 and U.S. Pat. No. 4,139,379, issued Feb. 13, 1979. Such nondiffusible RDR's can also be negative-working compounds, as described in U.S. Pat. Nos. 3,728,113 of Becker et al; 3,725,062 of Anderson and Lum; 3,698,897 of Gompf and Lum; 3,628,952 of Puschel et al; 3,443,939 and 3,443,940 of Bloom et al; 4,053,312 of Fleckenstein; 4,076,529 of Fleckenstein et al; 4,055,428 of Koyama et al; German Patents Nos. 2,505,248 and 2,729,820; *Reasearch Disclosure* 15157, November, 1976; and *Research Disclosure* 15654, April, 1977. In a more preferred embodiment of our invention, the nondiffusible RDR's are ballasted p-sulfonamidonaphthol compounds, each of which has a color-providing moiety attached thereto through a sulfonamido group which is alkali-cleavable upon oxidation.

A process for producing a photographic image in color according to our invention comprises:

treating an imagewise-exposed photographic element, as described above, with an alkaline processing composition in the presence of a silver halide developing agent to effect development of each exposed silver halide emulsion layer, whereby:

(a) an imagewise distribution of dye is formed as a function of the development of the silver halide emulsion layer; and (b) at least a portion of the imagewise distribution of the dye diffuses out of the element, such as to a dye image-receiving layer.

The above process is performed in the presence of the development restrainer precursor described above. During processing, the carbamoyl substituent is split off of the azole compound to provide the development restrainer, i.e., a compound according to formula I above is hydrolyzed by the aqueous alkaline processing composition to form the development restrainer:

Z being defined as above, which may be ionized in the composition.

It will be appreciated that, after processing the photographic elements described above, there remains in the elements, after transfer has taken place, an imagewise distribution of dye in addition to developed silver. A color image comprising residual nondiffusible compound may be obtained in these elements if the residual silver and silver halide are removed in any conventional manner well known to those skilled in the photographic art, such as a bleach bath followed by a fix bath, a bleach-fix bath, etc. The image-wise distribution of dye may also diffuse out of these elements into these baths, if desired, rather than to an image-receiving element.

The photographic element in the above-described process can be treated with an alkaline processing composition to effect or initiate development in any manner. One method for applying processing composition is by use of a rupturable container or pod which contains the composition. In general, the processing composition employed in this invention contains the developing agent for development, although the composition could also be solely an alkaline solution where the developer is incorporated in the photographic element, the image-receiving element or the process sheet, in which case the alkaline solution serves to activate the incorporated developer.

A photographic film unit or assemblage in accordance with this invention is adapted to be processed by an alkaline processing composition, and comprises:

(1) a photographic element as described above; and (2) a dye image-receiving layer.

In this embodiment, the processing composition may be inserted into the film unit, such as by interjecting processing solution with communicating members similar to hypodermic syringes which are attached either to a camera or camera cartridge. The processing composition may also be applied by means of a swab or by dipping in a bath, if so desired. The development restrainer precursors described above may be incorporated into the photographic element, as described above, or may be incorporated into the dye image-receiving layer or any layer associated therewith.

In another embodiment of the invention, the assemblage itself contains the alkaline processing composition and means containing same for discharge within the film unit, such as a rupturable container which is adapted to be positioned during processing of the film unit so that a compressive force applied to the container by pressure-applying members, such as would be found in a camera designed for in-camera processing, will effect a discharge of the container's contents within the film unit.

The dye image-receiving layer in the above-described film unit can be located on a separate support adapted to be superposed on the photographic element after exposure thereof. Such image-receiving elements are generally disclosed, for example, in U.S. Pat. No. 3,362,819. When the means for discharging the processing composition is a rupturable container, it is usually positioned in relation to the photographic element and the image-receiving element so that a compressive force applied to the container by pressure-applying members, such as would be found in a typical camera used for in-camera processing, will effect a discharge of the container's contents between the image-receiving element and the outermost layer of the photographic element. After processing, the dye image-receiving element is separated from the photographic element.

The dye image-receiving layer in the above-described film unit can also be located integral with the photographic element between the support and the lower-most photosensitive silver halide emulsion layer. One useful format for integral receiver-negative photographic elements is disclosed in Belgian Patent No. 757,960. In such an embodiment, the support for the photographic element is transparent and is coated with an image-receiving layer, a substantially opaque light-reflective layer e.g., $TiO_2$, and then the photosensitive layer or layers described above. After exposure of the photographic element, a rupturable container containing an alkaline processing composition and an opaque process sheet are brought into superposed position. Pressure-applying members in the camera rupture the container and spread processing composition over the photographic element as the film unit is withdrawn from the camera. The processing composition develops each exposed silver halide emulsion layer, and dye images, formed as a function of development, diffuse to the image-receiving layer to provide a positive, right-reading image which is viewed through the transparent support on the opaque reflecting layer background. For other details concerning the format of this particular integral film unit, reference is made to the above-mentioned Belgian Patent No. 757,960.

Another format for integral negative-receiver photographic elements in which the present invention can be employed is disclosed in Belgian Patent No. 757,959. In this embodiment, the support for the photographic element is transparent and is coated with the image-receiving layer, a substantially opaque, light-reflective layer and the photo-sensitive layer or layers described above. A rupturable container, containing an alkaline processing composition and an opacifier, is positioned between the top layer and a transparent cover sheet which has thereon a neutralizing layer and a timing layer. The film unit is placed in a camera, exposed through the transparent cover sheet and then passed through a pair of pressure-applying members in the camera as it is being removed therefrom. The pressure-applying members rupture the container and spread processing composition and opacifier over the negative portion of the film unit to render it light-insensitive. The processing composition develops each silver halide layer and dye images, formed as a result of development, diffuse to the image-receiving layer to provide a positive, right-reading image which is viewed through the transparent support on the opaque reflecting layer background. For further details concerning the format of this particular integral film unit, reference is made to the above mentioned Belgian Patent No. 757,959.

Still other useful integral formats in which this invention can be employed are described in U.S. Pat. Nos. 3,415,644; 3,415,645; 3,415,646; 3,647,437; and 3,635,707. In most of these formats, a photosensitive silver halide emulsion is coated on an opaque support, and a dye image-receiving layer is located on a separate transparent support superposed over the layer outermost from the opaque support. In addition, this transparent support also preferably contains a neutralizing layer and a timing layer underneath the dye image-receiving layer.

Another embodiment of the invention uses the image-reversing technique disclosed in British Pat. No. 904,364, page 19, lines 1 through 41. In this process, the dye-releasing compounds are used in combination with physical development nuclei in a nuclei layer contiguous to the photo-sensitive silver halide negative emulsion layer. The film unit contains a silver halide solvent, preferably in a rupturable container with the alkaline processing composition.

The film unit or assembly of the present invention may be used to produce positive images in single- or multi-colors. In a three-color system, each silver halide emulsion layer of the film assembly will have associated therewith a dye image-providing material which possesses a predominant spectral absorption within the region of the visible spectrum to which said silver halide emulsion is sensitive, i.e., the blue-sensitive silver halide emulsion layer will have a yellow dye image-providing material associated therewith, the green-sensitive silver halide emulsion layer will have a magenta dye image-providing material associated therewith, and the red-sensitive silver halide emulsion layer will have a cyan dye image-providing material associated therewith. The dye image-providing material associated with each silver halide emulsion layer may be contained either in the silver halide emulsion layer itself or in a layer contiguous to the silver halide emulsion layer, i.e., the dye image-providing material may be coated in a separate layer underneath the silver halide emulsion layer with respect to the exposure direction.

The concentration of the dye image-providing material that is employed in the present invention may be varied over a wide range, depending upon the particular compound employed and the results desired. For example, the dye image-providing material may be coated in a layer at a concentration of 0.1 to 3 $g/m^2$. The dye image-providing material may be dispersed in a hydrophilic film-forming natural material or synthetic polymer, such as gelatin, polyvinyl alcohol, etc, which is adapted to be permeated by aqueous alkaline processing composition.

A variety of silver halide developing agents can be employed in this invention. Specific examples of developers or ETA compounds which can be employed in this invention include hydroquinone compounds, such as hydroquinone, 2,5-dichlorohydroquinone, 2-chlorohydroquinone and the like; aminophenol compounds, such as 4-aminophenol, N-methylaminophenol, N,N-dimethylaminophenol, 3-methyl-4-aminophenol, 3,5-dibromoaminophenol and the like; catechol compounds, such as catechol, 4-cyclohexylcatechol, 3-methoxycatechol, 4-(N-octadecylamino)catechol and the like; phenylenediamine compounds, such as N,N-diethyl-p-phenylenediamine, 3-methyl-N,N-diethyl-p-phenylenediamine, 3-methoxy-N-ethyl-N-ethoxy-p-phenylenediamine, N,N,N',N'-tetramethyl-p-phenylenediamine and the like. In highly preferred embodiments, the ETA is a 3-pyrazolidinone compound, such as 1-phenyl-3-pyrazolidinone (Phenidone), 1-phenyl-4,4-dimethyl-3-pyrazolidinone (Dimezone), 4-hydroxymethyl-4-methyl-1-phenyl-3-pyrazolidinone, 4-hydroxymethyl-4-methyl-1-p-tolyl-3-pyrazolidinone, 4-hydroxymethyl-4-methyl-1-(3,4-dimethylphenyl)-3-pyrazolidinone, 1-m-tolyl-3-pyrazolidinone, 1-p-tolyl-3-pyrazolidinone, 1-phenyl-4-methyl-3-pyrazolidinone, 1-phenyl-5-methyl-3-pyrazolidinone, 1-phenyl-4,4-dihydroxymethyl-3-pyrazolidinone, 1,4-dimethyl-3-pyrazolidinone, 4-methyl-3-pyrazolidinone, 4,4-dimethyl-3-pyrazolidinone, 1-(3-chlorophenyl)-4-methyl-3-pyrazolidinone, 1-(4-chlorophenyl)-4-methyl-3-pyrazolidinone, 1-(3-chlorophenyl)-3-pyrazolidinone, 1-(4-chlorophenyl)-3-pyrazolidinone, 1-(4-tolyl)-4-methyl-3-pyrazolidinone, 1-(2-tolyl)-4-methyl-3-pyrazolidinone, 1-(4-tolyl)-3-pyrazolidinone, 1-(3-tolyl)-3-pyrazolidinone, 1-(3-tolyl)-4,4-dimethyl-3- pyrazolidinone, 1-(2-trifluoroethyl)-4,4-dimethyl-3-pyrazolidinone, 5-methyl-3-pyrazolidinone, and the like. A combination of different ETA's, such as those disclosed in U.S. Pat. No. 3,039,869, can also be employed. Such developing agents can be employed in the liquid processing composition or may be contained, at least in part, in any layer or layers of the photographic element or film unit to be activated by the alkaline processing composition, such as in the silver halide emulsion layers, the dye image-providing material layers, interlayers, image-receiving layer, etc.

In using dye image-providing materials in the invention which produce diffusible dye images as a function of development, either conventional negative-working or direct-positive silver halide emulsions may be employed. If the silver halide emulsion employed is a direct-positive silver halide emulsion, such as an internal-image emulsion designed for use in the internal image reversal process, or a fogged, direct-positive emulsion such as a solarizing emulsion, which is developable in unexposed areas, a positive image can be obtained on the dye image-receiving layer by using ballasted, redox, dye-releasers. After exposure of the film unit, the alkaline processing composition permeates the various layers to initiate development of the exposed photosensitive silver halide emulsion layers. The developing agent present in the film unit develops each of the silver halide emulsion layers in the unexposed areas (since the silver halide emulsions are direct-positive ones), thus causing the developing agent to become oxidized imagewise corresponding to the unexposed areas of the direct-positive silver halide emulsion layers. The oxidized developing agent then cross-oxidizes the dye-releasing compounds and the oxidized form of the compounds then undergoes a base-catalyzed reaction to release the dyes imagewise as a function of the imagewise exposure of each of the silver halide emulsion layers. At least a portion of the imagewise distributions of diffusible dyes diffuse to the image-receiving layer to form a positive image of the original subject. After being contacted by the alkaline processing composition, a pH-lowering layer in the film unit or image-receiving unit lowers the pH of the film unit or image receiver to stabilize the image.

Internal-image silver halide emulsions useful in this invention are described more fully in the November 1976 edition of *Research Disclosure*, pages 76 through 79, the disclosure of which is hereby incorporated by reference.

The various silver halide emulsion layers of a color film assembly employed in this invention can be disposed in the usual order, i.e., the blue-sensitive silver halide emulsion layer first with respect to the exposure side, followed by the green-sensitive and red-sensitive silver halide emulsion layers. If desired, a yellow dye layer or a yellow colloidal silver layer can be present between the blue-sensitive and green-sensitive silver halide emulsion layers for absorbing or filtering blue radiation that may be transmitted through the blue-sensitive layer. If desired, the selectively sensitized silver halide emulsion layers can be disposed in a different order, e.g., the blue-sensitive layer first with respect to the exposure side, followed by the red-sensitive and green-sensitive layers.

The rupturable container employed in certain embodiments of this invention can be of the type disclosed in U.S. Pat. Nos. 2,543,181; 2,643,886; 2,653,732; 2,723,051; 3,056,492; 3,056,491 and 3,152,515. In general, such containers comprise a rectangular sheet of fluid- and air-impervious material folded longitudinally upon itself to form two walls which are sealed to one another along their longitudinal and end margins to form a cavity in which processing solution is contained.

Generally speaking, except where noted otherwise, the silver halide emulsion layers employed in the invention comprise photosensitive silver halide dispersed in gelatin and are about 0.6 to 6 microns in thickness; the dye image-providing materials are dispersed in an aqueous alkaline solution-permeable polymeric binder, such as gelatin, as a separate layer about 0.2 to 7 microns in thickness; and the alkaline solution-permeable polymeric interlayers, e.g., gelatin, are about 0.2 to 5 microns in thickness. Of course, these thicknesses are approximate only and can be modified according to the product desired.

Any material can be employed as the image-receiving layer in this invention as long as the desired function of mordanting or otherwise fixing the dye images is obtained. The particular material chosen will, of course, depend upon the dye to be mordanted. Suitable materials are disclosed on pages 80 through 82 of the November 1976 edition of *Research Disclosure*, the disclosure of which is hereby incorporated by reference.

Use of a pH-lowering material in the film units of this invention will usually increase the stability of the transferred image. Generally, the pH-lowering material will effect a reduction in the pH of the image layer from about 13 or 14 to at least 11 and preferably 5 to 8 within a short time after imbibition. Suitable materials and their functions are disclosed on pages 22 and 23 of the July 1974 edition of *Research Disclosure*, and pages 35 through 37 of the July 1975 edition of *Research Disclosure*, the disclosures of which are hereby incorporated by reference.

A timing or inert spacer layer can be employed in the practice of this invention over the pH-lowering layer which "times" or controls the pH reduction as a function of the rate at which the alkaline composition diffuses through the inert spacer layer. Examples of such timing layers and their functions are disclosed in the *Research Disclosure* articles mentioned in the paragraph above concerning pH-lowering layers.

The alkaline processing composition employed in this invention is the conventional aqueous solution of an alkaline material, e.g., alkali metal hydroxides or carbonates such as sodium hydroxide, sodium carbonate or an amine such as diethylamine, preferably possessing a pH in excess of 11, and preferably containing a developing agent as described previously. Suitable materials and addenda frequently added to such compositions are disclosed on pages 79 and 80 of the November 1976 edition of *Research Disclosure*, the disclosure of which is hereby incorporated by reference.

The alkaline solution-permeable, substantially opaque, light-reflective layer employed in certain embodiments of photographic film units used in this invention are described more fully in the November 1976 edition of *Research Disclosure*, page 82, the disclosure of which is hereby incorporated by reference.

The supports for the photographic elements used in this invention can be any material, as long as it does not deleteriously affect the photographic properties of the film unit and is dimensionally stable. Typical flexible sheet materials are described on page 85 of the November 1976 edition of *Research Disclosure*, the disclosure of which is hereby incorporated by reference.

While the invention has been described with reference to layers of silver halide emulsions and dye image-providing materials, dotwise coating, such as would be obtained using a gravure printing technique, could also be employed. In this technique, small dots of blue-, green- and red-sensitive emulsions have associated therewith, respectively, dots of yellow, magenta and cyan color-providing substances. After development, the transferred dyes would tend to fuse together into a continuous tone.

The silver halide emulsions useful in this invention, both negative-working and direct-positive ones, are well known to those skilled in the art and are described in Research Disclosure, Volume 176, December 1978, Item 17643, pages 22 and 23, "Emulsion preparation and types"; they may be chemically and spectrally sensitized as described on page 23, "Chemical sensitization", and "Spectral sensitization and desensitization", of the above article; they can be protected against the production of fog and can be stabilized against loss of sensitivity during keeping by employing the materials described on pages 24 and 25, "Antifoggants and stabilizers", of the above article; they can contain hardeners and coating aids as described on page 26, "Hardeners", and pages 26 and 27, "Coating aids", of the above article; they and other layers in the photographic elements used in this invention can contain plasticizers, vehicles and filter dyes described on page 27, "Plasticizers and lubricants", page 26, "Vehicles and vehicle extenders", and pages 25 and 26, "Absorbing and scattering materials", of the above article; they and other layers in the photographic elements used in this invention may contain addenda which are incorporated by using the procedures described on page 27, "Methods of addition", of the above article; and they can be coated and dried by using the various techniques described on pages 27 and 28, "Coating and drying procedures", of the above article, the disclosures of which are hereby incorporated by reference.

The term "nondiffusing" used herein has the meaning commonly applied to the term in photography and denotes materials that for all practical purposes do not migrate or wander through organic colloid layers, such as gelatin, in the photographic elements of the invention in an alkaline medium and preferably when processed in a medium having a pH of 11 or greater. The same meaning is to be attached to the term "immobile". The term "diffusible" as applied to the materials of this invention has the converse meaning and denotes materials having the property of diffusing effectively through the colloid layers of the photographic elements in an alkaline medium. "Mobile" has the same meaning as "diffusible".

The term "associated therewith" as used herein is intended to mean that the materials can be in either the same or different layers so long as the materials are accessible to one another.

The following examples are provided to further illustrate the invention.

EXAMPLE 1

Preparation of Compound 1

Compound 1: 1-(N-Ethyl-N-phenylcarbamoyl)-5-methylbenzotriazole

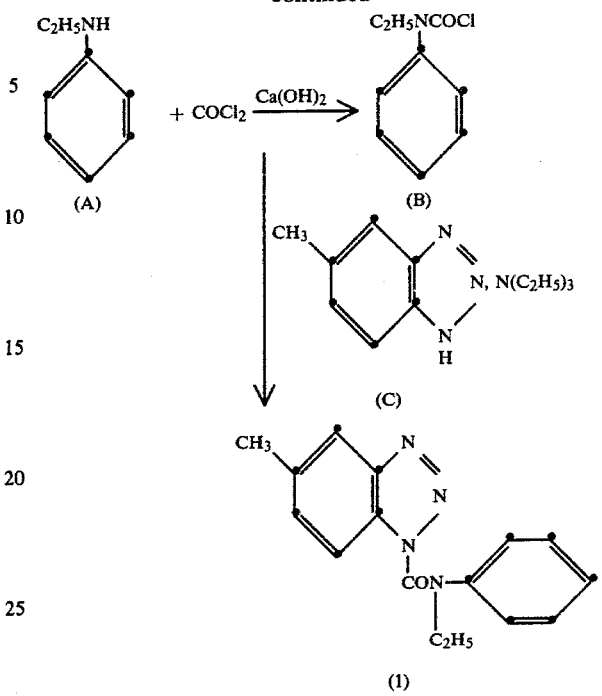

(a) N-Ethyl-N-phenylcarbamoyl chloride (B)

This was prepared by the method of Carpino and Cowecke (L. A. Carpino and S. Gowecke, J. Org. Chem., 29, 2824, 1964), in 60 percent yield, m.p. 44° to 45° C. (uncorr.).

(b) 1-(N-Ethyl-N-phenylcarbamoyl)-5-methylbenzotriazole (1)

5-Methylbenzotriazole (C) (13.3 g, 0.1 mole) was suspended in triethylamine (100 ml) and N-ethyl-N-phenylcarbamoyl chloride (B) (18.35 g, 0.1 mole) was added in small portions, with stirring. The resultant mixture was heated under reflux for 2 hours, cooled, and the solvent was removed under reduced pressure. The residue was taken up in water (200 ml) and dichloromethane (200 ml) and the organic layer was separated. This was washed with dilute hydrochloric acid (3 molar, 1×200 ml), dried (magnesium sulfate) and the solvent was removed to leave an oil which crystallized from a cyclohexane:petroleum ether (b.p. 40° to 60° C.) mixture (1:1.5 v/v) to give a colorless solid (21.72 g, 78 percent), m.p. 42° to 43° C. (uncorr.), which is (1) and the 6-methyl isomer.

$C_{16}H_{16}N_4O$ Requires: C, 68.55; H, 5.75; N, 19.99%. Found: C, 68.11; H, 5.81; N, 19.86%.

EXAMPLE 2

Preparation of Compound 2

Compound 2: 1-(N-Morpholinocarbonyl)-5-methylbenzotriazole

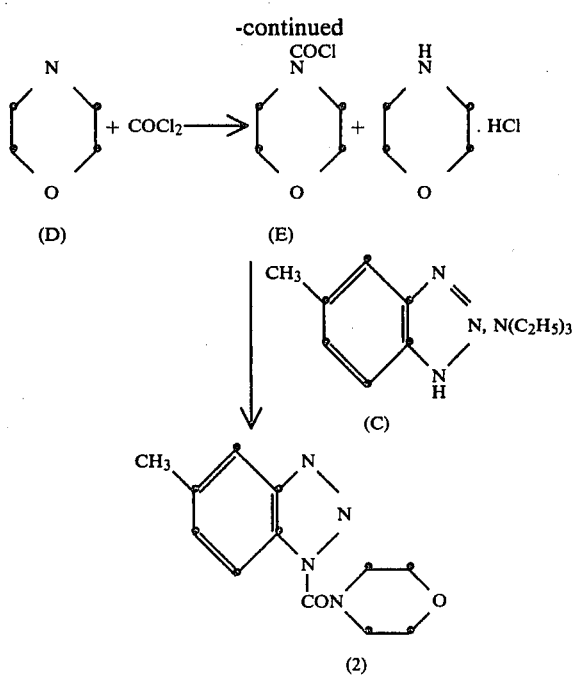

(a) Morpholinocarbonyl chloride (E)

This was prepared by the method of Boon (W. R. Boon, J.C.S., 307, 1947), in 66 percent yield, b.p. 105° to 107° C./7.5 mm.

(b) 1-Morpholinocarbonyl-5-methylbenzotriazole (2)

Compound 2 was prepared by treating 5-methylbenzotriazole (C) (8.89 g, 67 m.mole) with morpholinocarbamoyl chloride (E) (10 g, 67 m.mole) in a manner similar to that described in the preparation of (1). The product which included the 6-methyl isomer was crystallized from methanol (100 ml). Yield, 13.2 g, 81 percent, m.p. 81° to 82° C. (uncorr.).

$C_{12}H_{14}N_4O_2$ Requires: C, 58.52; H, 5.73; N, 22.75%. Found: C, 58.33; H, 5.73; N, 22.97%.

Other examples which were prepared via the method used for Compound 2 include:

EXAMPLE 3

Preparation of Compound 3

Compound 3: 1-Piperidinocarbonyl-5-methylbenzotriazole

This was prepared in 73 percent yield, (including the 6-methyl isomer), m.p. 49° to 50° C. (uncorr.) from petroleum ether (b.p. 40° to 60° C.).

$C_{13}H_{16}N_4O$ Requires: C, 63.91; H, 6.60; N, 22.94%. Found: C, 63.53; H, 6.60; N, 22.87%.

EXAMPLE 4

Preparation of Compound 4

Compound 4: 1-(N,N-diphenylcarbamoyl)-5-methylbenzotriazole

This was prepared in 76 percent yield, (including the 6-methyl isomer), m.p. 132° to 133° C. (uncorr., from methanol).

$C_{20}H_{16}N_4O$ Requires: C, 73.15; H, 4.91; N, 17.06%. Found: C, 72.85; H, 5.03; N, 17.28%.

EXAMPLE 5

Preparation of Compound 8

Compound 8: 1-Morpholinocarbonyl-5,6-dimethylbenzotriazole

This was prepared in 61 percent yield, m.p. 191° C. (uncorr., from methanol).

$C_{13}H_{16}N_4O_2$ Requires: C, 59.99; H, 6.20; N, 21.53%. Found: C, 59.82; H, 6.20; N, 22.27%.

EXAMPLE 6

Preparation of Compound 10

Compound 10: 1-Morpholinocarbonyl-4,6-dimethylbenzotriazole

This was prepared in 64 percent yield including the 5,7-dimethyl isomer, m.p. 115° C. (uncorr., from methanol).

$C_{13}H_{16}N_4O_2$ Requires: C, 59.99; H, 6.20; N, 21.53%. Found: C, 59.10; H, 6.12; N, 21.77%.

EXAMPLE 7

Preparation of Compound 12

Compound 12: 1-Morpholinocarbonyl-5,6-dichlorobenzotriazole

This was prepared in 64 percent yield, m.p. 145° C. (uncorr., from methanol).

$C_{11}H_{10}Cl_2N_4O_2$ Requires: C, 43.87; H, 3.35; Cl, 23.54; N, 18.61%. Found: C, 43.75; H, 3.40; Cl, 24.76; N, 18.80%.

EXAMPLE 8

Preparation of Compound 15

Compound 15: 2-Morpholinocarbonyl-4,5,6,7-tetrachlorobenzotriazole

This was prepared in 50 percent yield, m.p. 194° C. (uncorr., from methanol).

$C_{11}H_8Cl_4N_4O_2$ Requires: C, 35.71; H, 2.18; Cl, 38.32; N, 15.14%. Found: C, 35.64; H, 2.17; Cl, 38.00; N, 15.50%.

EXAMPLE 9

Preparation of Compound 6

Compound 6: Ethyl 11-[N-(5-methyl-1-benzotriazolylcarbonyl)N-ethyl-]aminoundecanoate This was prepared in 88 percent yield (including the 6-methyl isomer) as an oil after chromatographic purification.

$C_{23}H_{36}N_4O_3$ Requires: C, 66.32; H, 8.71; N, 13.45%. Found: C, 66.26; H, 8.62; N, 13.55%.

Other compounds which were prepared in two stages via the method used for compound 1 include:

EXAMPLE 10

Preparation of Compound 5

Compound 5: 1-(N-Ethyl-N-(4-methoxyphenyl)-5-methylbenzotriazole

This was prepared in 67 percent yield, (including the 6-methyl isomer), m.p. 75° C. (uncorr., from cyclohexane:petroleum ether) (40° to 60° C.) (1:4).

$C_{17}H_{18}N_4O_2$ Requires: C, 65.79; H, 5.85; N, 18.05. Found: C, 65.45; H, 5.92; N, 17.93.

EXAMPLE 11

Preparation of Compound 9

Compound 9:
1-(N-Ethyl-N-phenylcarbamoyl)-5,6-dimethylbenzo-triazole

This was prepared in 81 percent yield, m.p. 136° C. (uncorr., from methanol).

$C_{17}H_{18}N_4O$ Requires: C, 69.37; H, 6.16; N, 19.04%. Found: C, 69.12; H, 6.21; N, 19.28%.

EXAMPLE 12

Preparation of Compound 11

Compound 11:
1-(N-Ethyl-N-phenylcarbamoyl)-5,7-dimethylbenzo-triazole

This was prepared in 71 percent yield, (including the 4,6-dimethyl isomer), m.p. 90° C. (uncorr., from methanol).

$C_{17}H_{18}N_4O$ Requires: C, 69.37; H, 6.16; N, 19.04%. Found: C, 69.33; H, 6.20; N, 19.48%.

EXAMPLE 13

Preparation of Compound 13

Compound 13:
1-(N-Ethyl-N-phenylcarbamoyl)-5,6-dichlorobenzo-triazole

This was prepared in 88 percent yield, m.p. 120° C. (uncorr., from cyclohexane).

$C_{15}H_{12}Cl_2N_4O$ Requires: C, 53.75; H, 3.61; Cl, 21.15; N, 16.72%. Found: C, 53.79; H, 3.74; Cl, 21.18; N, 16.92%.

EXAMPLE 14

Preparation of Compound 16

Compound 16:
2-(N-Ethyl-N-phenylcarbamoyl)-4,5,6,7-tetra-chlorobenzotriazole

This was prepared in 86 percent yield, m.p. 157° C. (uncorr., from cyclohexane).

$C_{15}H_{10}Cl_4N_4O$ Requires: C, 44.59; H, 2.49; Cl, 35.09; N, 13.87%. Found: C, 44.65; H, 2.50; Cl, 35.18; N, 14.15%.

EXAMPLE 15

Preparation of Compound 7

Compound 7: Ethyl 11-[1-(N-Ethyl-N-phenylcarbamoyl)-6-benzo-triazolecarbonamido]undecanoate This was prepared in 87 percent yield as a white oily solid after chromatographic purification.

$C_{29}H_{39}N_5O_4$ Requires: C, 66.28; H, 7.48; N, 13.32%. Found: C, 66.77; H, 7.54; N, 13.42%.

EXAMPLE 16

Preparation of Compound 14

Compound 14:
5,6-Dichloro-1-dimethylcarbamoylbenzotriazole

In 100 ml of dry tetrahydrofuran, 1.2 g of sodium hydride is suspended. To this mixture, a solution of 9.4 g of 5,6-dichlorobenzotriazole in 250 ml of tetrahydrofuran is added with vigorous stirring. After it is stirred at room temperature for 30 minutes, 5.4 g of N,N-dimethylcarbamoyl chloride is added, and the reaction mixture is refluxed for 15 minutes, then allowed to gradually come to room temperature. The sodium chloride salt formed is removed; the solution is treated with charcoal and filtered. The solvent is evaporated to yield a white, solid residue. Recrystallization from aqueous methanol yields 6.7 g (51.9 percent) of colorless solid; m.p. 120° to 123° C.

$C_9H_8Cl_2N_4O$ Requires: C, 41.7; H, 3.1; N, 21.7. Found: C, 42.2; H, 3.3; N, 21.6.

EXAMPLE 17

The rates of hydrolysis of the development restrainer precursors in alkaline solution were estimated as follows:

A silver-silver chloride electrode was freshly prepared by electrolysis of a clean silver rod in 0.5 M aqueous potassium chloride solution. This electrode, together with a standard calomel reference electrode, was connected to a pH meter whose output was recorded on a chart recorder. The electrodes were immersed in a stirred solution at room temperature of composition: 10 percent v/v ethanol, 90 percent water, 0.1 M sodium hydroxide, and 0.01 M potassium chloride. The volume of the solution was 50 ml. A solution of development restrainer precursor (2 ml of 0.4 M solution in ethanol) was added rapidly from a syringe, and the resulting perturbation of the electrical potential given by the electrode pair was recorded as a function of time. When 5-methylbenzotriazole was added, the time taken for the potential to reach 60 percent of the difference between the final and initial readings (which should approximately correspond to 50 percent adsorption of the benzotriazole at the electrode) was about 3 seconds. This is taken as the response time of the measuring system.

In this way, estimates were made of the $t_{\frac{1}{2}}$ value (time for half the added development restrainer precursor to be hydrolyzed to the development restrainer) for the various compounds of the invention. The values found are given in Table I. The letter I by a value indicates that the compound was largely insoluble in the solution, giving a greater $t_{\frac{1}{2}}$ value than would otherwise be the case.

TABLE I

| Compound No. | Hydrolysis $t_{\frac{1}{2}}$ (seconds) |
| --- | --- |
| 1 | >300 I |
| 2 | 15 |
| 3 | 65 |
| 4 | >300 I |
| 5 | >300 I |
| 6 | >300 I |
| 7 | >300 I |
| 8 | 11 |
| 9 | >300 I |
| 10 | 9 |
| 11 | >300 I |
| 12 | 30 I |
| 13 | >300 I |
| 15 | 180 I |
| 16 | >600 I |

EXAMPLE 18

Photographic Test (i) Preparation of receiver sheets (a) A receiver sheet was prepared by coating an aqueous solution (pH 6.5) onto polyethylene-coated paper to give the following coated layer (concentrations are in grams per square meter unless otherwise stated):
  gelatin: 2.2
  polyvinylimidazole (10 percent quaternized with 2-chloroethanol): 2.2
  4-hydroxymethyl-4-methyl-1-phenyl-3-pyrazolidone: 0.22
  piperidine hydrochloride: 0.09
  formaldehyde: 0.04

This receiver (a) constitutes a control.

(b) Another receiver was prepared as (a), but with the addition of a fine dispersion of prior art compound [1-cyclohexylcarbamoyl-5(6)-methylbenzotriazole] (0.27) dissolved in droplets of diethyl lauramide (0.79).

(c) Another receiver was prepared similar to (a), but with the addition of a solution in acetone of Compound 1 (0.48) of the invention.

(d) Another receiver was prepared similar to (a), but with the addition of a solution, in tetrahydrofuran, of Compound 2 (0.32) of the invention.

(ii) Preparation of Photosensitive Element

A photosensitive element was prepared by coating the following layers in the order recited on a poly(ethylene terephthalate) film support. Quantities are parenthetically given in grams per square meter unless otherwise stated.

(1) red-sensitive, negative-working, 15:85 silver chlorobromide emulsion (silver 0.59, gelatin 1.35) and cyan RDR A (0.44) dispersed in 1,4-cyclohexylenedimethylene-bis(2-ethylhexanoate) (0.22);

(2) interlayer of gelatin (1.35) and 2,5-di-sec-dodecylhydroquinone (0.97);

(3) magenta RDR B (0.44) dispersed in 1,4-cyclohexylenedimethylene-bis(2-ethylhexanoate) (0.22) and gelatin (1.35);

(4) green-sensitive, negative-working, 15:85 silver chlorobromide emulsion (silver 0.95, gelatin 1.35);

(5) interlayer of gelatin (1.35) and 2,5-di-sec-dodecylhydroquinone (0.83);

(6) yellow RDR C (1.12) dispersed in 1,4-cyclohexylenedimethylene-bis(2-ethylhexanoate) (0.56), gelatin (1.43), and bis(vinylsulfonylmethyl) ether (0.11);

(7) blue-sensitive, negative-working, 15:85 silver chlorobromide emulsion (silver 1.18, gelatin 1.35) and 2,5-di-sec-dodecylhydroquinone (0.1); and (8) gelatin (1.35) and copoly[styrene(N,N-dimethyl-N-benzyl-N-3-maleimidopropyl)ammonium chloride] (0.1).

CYAN RDR A

MAGENTA RDR B

YELLOW RDR C (iii) Testing of Receiver Sheets

Portions of the photosensitive element of (ii) were exposed to a sensitometric light source. They were soaked in the activator solution described below at 30° C. for 15 seconds, then withdrawn and squeegeed into intimate face-to-face contact with a portion of the receiver sheet of (i).

| Activator Solution | |
|---|---|
| potassium hydroxide | 37 g |
| benzyl alcohol | 10 ml |
| 11-aminoundecanoic acid | 2 g |
| 6-aminohexanoic acid | 15 g |
| 5-methylbenzotriazole | 1 g |
| water to | 1 liter |

The coatings were peeled apart after 2.5 and 5 minutes process time. A negative dye image was visible on the receiving sheets. The reflection densities in unexposed ($D_{min}$) and in fully exposed ($D_{max}$) areas were read through red, green and blue filters. The results are given in Table II. Δ signifies the difference between the density at 5 minutes and the density at 2.5 minutes.

TABLE II

| Receiver | Development Restrainer | Time (minutes) | $D_{min}$ Red | Green | Blue | Red | $D_{max}$ Green | Blue |
|---|---|---|---|---|---|---|---|---|
| (a) control | None | 2.5 | 0.11 | 0.15 | 0.18 | 2.51 | 2.19 | 2.78 |
|  |  | 5 | 0.18 | 0.20 | 0.30 | 2.57 | 2.24 | 3.20 |
|  |  | Δ | 0.07 | 0.05 | 0.12 | 0.08 | 0.05 | 0.42 |
| (b) control | prior art compound | 2.5 | 0.12 | 0.16 | 0.19 | 2.08 | 1.78 | 2.38 |
|  |  | 5 | 0.16 | 0.18 | 0.24 | 2.68 | 2.06 | 2.74 |
|  |  | Δ | 0.04 | 0.02 | 0.05 | 0.60 | 0.28 | 0.36 |
| (c) | Compound 1 | 2.5 | 0.13 | 0.17 | 0.16 | 2.29 | 2.09 | 2.17 |
|  |  | 5 | 0.16 | 0.20 | 0.21 | 2.56 | 2.17 | 2.41 |
|  |  | Δ | 0.03 | 0.03 | 0.05 | 0.27 | 0.08 | 0.24 |
| (d) | Compound 2 | 2.5 | 0.12 | 0.15 | 0.16 | 2.56 | 2.20 | 2.34 |
|  |  | 5 | 0.18 | 0.18 | 0.21 | 3.16 | 2.42 | 2.87 |
|  |  | Δ | 0.06 | 0.03 | 0.05 | 0.60 | 0.28 | 0.53 |

The results show that all of the development restrainer precursors limited the growth of minimum density compared with control (a). However, the rapid release of the prior art compound resulted in undue suppression of the red and green $D_{max}$ at the shorter time of lamination. The compounds of the invention, however, gave similar control of $D_{min}$ without so much suppression of $D_{max}$.

EXAMPLE 19

Photographic Test (i) Preparation of Receiver Sheets (e) A receiver sheet was prepared by separately coating and drying the following aqueous solutions (pH 5.5) on polyethylene coated paper (concentrations are in grams per square meter unless otherwise stated):

| Layer 1 | |
|---|---|
| gelatin | 2.2 |
| formaldehyde | 0.03 |
| Layer 2 | |
| polyvinylimidazole (10 percent quaternized with 2-chloroethanol) | 2.2 |
| 4-hydroxymethyl-4-methyl-1-phenyl-3-pyrazolidone | 0.22 |
| formaldehyde | 0.03 |

This receiver (e) constitutes a control.

(f) Another receiver was prepared similar to (e), except that Layer 1 was:
gelatin: 2.2
formaldehyde: 0.03
Compound 1: 0.81
N-n-butylacetanilide: 1.6
Aerosol OT (trademark) surfactant: 0.07

(ii) Preparation of Photosensitive Element

A photosensitive element was prepared by coating the following layers in the order recited on poly(ethylene terephthalate) film support. Quantities are parenthetically given in grams per square meter unless otherwise stated:

(1) cyan dye-providing layer of gelatin (1.5), cyan RDR D (0.45) dispersed in N,N-diethyl-lauramide (0.22), and bis(vinylsulfonylmethyl)ether (0.03);

(2) red-sensitive, direct-positive, 0.75 μm silver bromide emulsion (silver 0.35, gelatin 1.0), 1-dimethyl-3-[4-(2-formylhydrazino)phenyl]thiourea (10 mg/silver mol);

(3) interlayer of gelatin (1.0) and 2,5-di-sec-dodecylhydroquinone (0.5);

(4) magenta dye-providing layer of magenta RDR E (0.45) dispersed in N,N-diethyl-lauramide (0.22), gelatin (1.0) and bis(vinylsulfonylmethyl)ether (0.03);

(5) green-sensitive, direct-positive, 0.75 μm silver bromide emulsion (silver 0.35, gelatin 1.0), 1-methyl-3[4-(2-formylhydrazino)phenyl]thiourea (25 mg/silver mol);

(6) interlayer of gelatin (1.0) and 2,5-di-sec-dodecylhydroquinone (0.5);

(7) yellow dye-providing layer of yellow RDR F (0.5) dispersed in N,N-diethyl-lauramide (0.25), gelatin (1.0) and bis(vinylsulfonylmethyl)ether (0.03);

(8) blue-sensitive, direct-positive, 0.75 μm silver bromide emulsion (silver 0.35, gelatin 1.0), 1-methyl-3[4-(2-formylhydrazino)phenyl]thiourea (15 mg/silver mol); and (9) overcoat layer of gelatin (1.0) and copoly[styrene(N,N-dimethyl-N-benzyl-N-3-maleimidopropyl)ammonium chloride] (0.05).

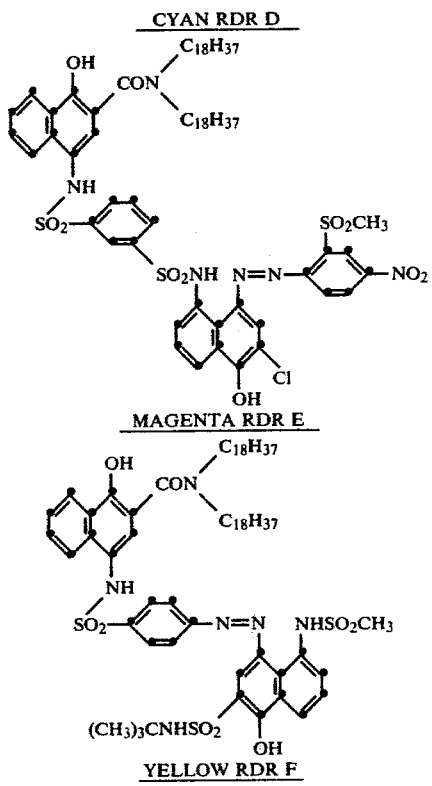

-continued

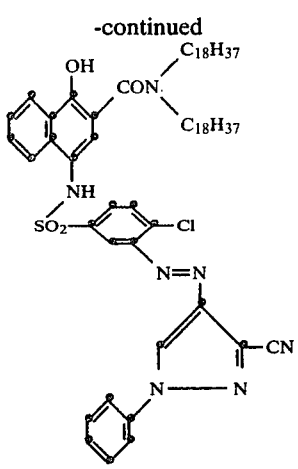

(iii) Testing of Receiver Sheets

Portions of the photosensitive element of (ii) were exposed to a sensitometric light source. They were soaked in the activator solution described below at 28° C. for 30 seconds, then withdrawn and squeegeed into intimate face-to-face contact with a portion of the receiver sheets of (i).

| Activator Solution | |
|---|---|
| potassium hydroxide | 42 g |
| benzyl alcohol | 10 ml |
| 5-methylbenzotriazole | 3 g |
| water to | 1 liter |

The coatings were peeled apart after 3.5 and 6 minutes at 21° C. A positive dye image was visible on the receiving sheets. The image was measured with a reflection densitometer through red, green and blue filters. In Table III are listed $D_{min}$ and speed values (speed equals—relative $Log_{10}$ exposure).

TABLE III

| Receiver | Development Restrainer | Time (minutes) | $D_{min}$ Red | $D_{min}$ Green | $D_{min}$ Blue | Speed Red | Speed Green | Speed Blue |
|---|---|---|---|---|---|---|---|---|
| (e) | None | 3.5 | 0.46 | 0.27 | 0.33 | 1.46 | 1.80 | 1.07 |
|  |  | 6 | 0.53 | 0.30 | 0.37 | 1.43 | 1.71 | 1.02 |
|  |  | Δ | 0.07 | 0.03 | 0.04 | −0.03 | −0.09 | −0.05 |
| (f) | Compound 1 | 3.5 | 0.46 | 0.27 | 0.35 | 1.47 | 1.82 | 1.06 |
|  |  | 6 | 0.50 | 0.30 | 0.37 | 1.46 | 1.86 | 1.07 |
|  |  | Δ | 0.04 | 0.03 | 0.02 | −0.01 | +0.04 | +0.01 |

The results show that the compound of the invention had the desired effect of minimizing sensitometric changes as the processing time was increased from 3.5 to 6 minutes.

The invention has been described in detail with particular reference to preferred embodiments thereof, but it will be understood that variations and modifications can be effected within the spirit and scope of the invention.

What is claimed is:

1. In a photographic element comprising a support having thereon at least one photosensitive silver halide emulsion layer having associated therewith a dye image-providing material, the improvement wherein said element contains a development restrainer azole compound having an alkali-hydrolyzable, N,N-disubstituted carbamoyl group, said compound having the following formula:

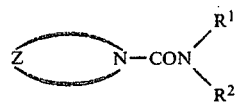

wherein:
$R^1$ and $R^2$ each represent a substituted or unsubstituted alicyclic, aliphatic, aromatic or heterocyclic moiety, or may be taken together with the nitrogen to which they are attached to form a heterocyclic ring; and Z represents the atoms necessary to complete an azole ring containing at least two nitrogen atoms.

2. The photographic element of claim 1 wherein said azole ring is a benzotriazole, triazole, tetrazole, imidazole or benzimidazole.

3. The photographic element of claim 1 wherein said azole ring is a benzotriazole.

4. The photographic element of claim 1 wherein said compound has either of the following formulas:

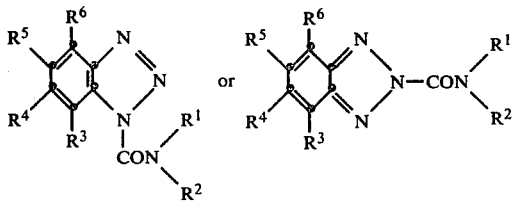

wherein:
$R^1$ and $R^2$ each represent a substituted or unsubstituted alicyclic, aliphatic, aromatic or heterocyclic moiety, or may be taken together with the nitrogen to which they are attached to form a heterocyclic ring; and $R^3$, $R^4$, $R^5$ and $R^6$ each represent hydrogen, nitro, lower alkyl, halogen, carbamoyl, sulfamoyl, RCONH— or $RSO_2NH$—, wherein R is lower alkyl or aryl.

5. The photographic element of claim 1 wherein each $R^1$ and $R^2$ is a substituted or unsubstituted alkyl or aryl group.

6. The photographic element of claim 1 wherein each $R^1$ and $R^2$ is ethyl, phenyl, 4-methoxyphenyl or —$(CH_2)_{10}$—$COOC_2H_5$, or $R^1$ and $R^2$ together complete a morpholine or piperidine ring.

7. The photographic element of claim 1 wherein said dye image-providing material is a ballasted, redoxdye-releasing compound.

8. The photographic element of claim 7 wherein said dye-releasing compound is a p-sulfonamidonaphthol.

9. The photographic element of claim 1 wherein said compound is:

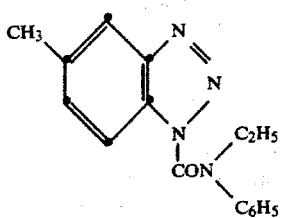

10. The photographic element of claim 1 wherein said compound is:

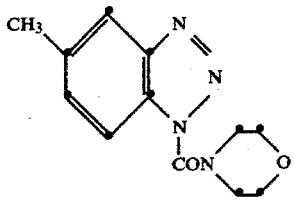

11. The photographic element of claim 1 wherein said photographic element comprises a support having thereon a red-sensitive silver halide emulsion layer having a cyan dye image-providing material associated therewith, a green-sensitive silver halide emulsion layer having a magenta dye image-providing material associated therewith, and a blue-sensitive silver halide emulsion layer having a yellow dye image-providing material associated therewith.

12. In a photographic assemblage to be processed by an alkaline processing composition, said assemblage comprising:
(a) a photographic element comprising a support having thereon at least one photosensitive silver halide emulsion layer having associated therewith a dye image-providing material; and
(b) a dye image-receiving layer;
the improvement wherein said assemblage contains a development restrainer azole compound having an alkali-hydrolyzable, N,N-disubstituted carbamoyl group, said compound having the following formula:

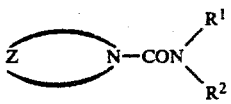

wherein:
R¹ and R² each represent a substituted or unsubstituted alicyclic, aliphatic, aromatic or heterocyclic moiety, or may be taken together with the nitrogen to which they are attached to form a heterocyclic ring; and
Z represents the atoms necessary to complete an azole ring containing at least two nitrogen atoms.

13. In a photographic assemblage comprising:
(a) a photographic element comprising a support having thereon at least one photosensitive silver halide emulsion layer having associated therewith a dye image-providing material;
(b) a dye image-receiving layer; and
(c) an alkaline processing composition and means containing same for discharge within said assemblage;
said assemblage containing a silver halide developing agent; the improvement wherein said assemblage contains a development restrainer azole compound having an alkali-hydrolyzable, N,N-disubstituted carbamoyl group, said compound having the following formula:

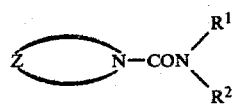

wherein:
R¹ and R² each represent a substituted or unsubstituted alicyclic, aliphatic, aromatic or heterocyclic moiety, or may be taken together with the nitrogen to which they are attached to form a heterocyclic ring; and
Z represents the atoms necessary to complete an azole ring containing at least two nitrogen atoms.

14. The photographic assemblage of claim 13 wherein said azole ring is a benzotriazole, triazole, tetrazole, imidazole or benzimidazole.

15. The photographic assemblage of claim 13 wherein said azole ring is a benzotriazole.

16. The photographic assemblage of claim 13 wherein said photographic element comprises a support having thereon a red-sensitive silver halide emulsion layer having associated therewith a cyan dye image-providing material, a green-sensitive silver halide emulsion layer having associated therewith a magenta dye image-providing material, and a blue-sensitive silver halide emulsion layer having associated therewith a yellow dye image-providing material.

17. The photographic assemblage of claim 13 wherein:
(a) said dye image-receiving layer is located between said support and said silver halide emulsion layer; and
(b) said assemblage also includes a transparent cover sheet over the layer outermost from said support.

18. The photographic assemblage of claim 17 wherein said cover sheet has thereon, in sequence, a neutralizing layer and a timing layer.

19. The photographic assemblage of claim 18 wherein said discharging means is a rupturable container containing said alkaline processing composition and an opacifying agent, said container being so positioned during processing of said assemblage that a compressive force applied to said container will effect a discharge of the container's contents between said transparent sheet and the layer outermost from said support.

20. The photographic assemblage of claim 13 wherein said support having thereon said photosensitive silver halide emulsion layer is opaque and said dye image-receiving layer is located on a separate transparent support superposed over the layer outermost from said opaque support.

21. The photographic assemblage of claim 20 wherein said transparent support has thereon, in sequence, a neutralizing layer, a timing layer and said dye image-receiving layer.

22. The photographic assemblage of claim 13 wherein said dye image-receiving layer is located on a separate support to form a receiving element, said receiving element being adapted to be superposed on said photosensitive element after exposure thereof.

23. The photographic assemblage of claim 22 wherein said receiving element contains said azole compound.

24. In a process for producing a photographic image in color in an imagewise-exposed photographic element comprising a support having thereon at least one photosensitive silver halide emulsion layer having associated therewith a dye image-providing material, said process comprising:

treating said element with an alkaline processing composition in the presence of a silver halide developing agent to effect development of each exposed silver halide emulsion layer, whereby:
(a) an imagewise distribution of said dye is formed as a function of said development of said silver halide emulsion layer; and
(b) at least a portion of said imagewise distribution of said dye diffuses out of said element,
the improvement wherein said process is performed in the presence of a development restrainer azole compound having an alkali-hydrolyzable, N,N-disubstituted carbamoyl group, said compound having the following formula:

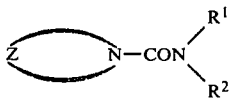

wherein:
$R^1$ and $R^2$ each represent a substituted or unsubstituted alicyclic, aliphatic, aromatic or heterocyclic moiety, or may be taken together with the nitrogen to which they are attached to form a heterocyclic ring; and
Z represents the atoms necessary to complete an azole ring containing at least two nitrogen atoms.

25. The process of claim 24 wherein said imagewise distribution of said dye diffuses to a dye image-receiving layer.

26. The process of claim 24 wherein said azole ring is a benzotriazole, triazole, tetrazole, imidazole or benzimidazole.

27. The process of claim 26 wherein said azole ring is a benzotriazole.

28. The process of claim 24 wherein said photographic element comprises a support having thereon a red-sensitive silver halide emulsion layer having a cyan dye image-providing material associated therewith, a green-sensitive silver halide emulsion layer having a magenta dye image-providing material associated therewith, and a blue-sensitive silver halide emulsion layer having a yellow dye image-providing material associated therewith.

29. In a dye image-receiving element comprising a support having thereon a dye image-receiving layer, the improvement wherein said element contains a development restrainer azole compound having an alkali-hydrolyzable, N,N-disubstituted carbamoyl group, said compound having the following formula:

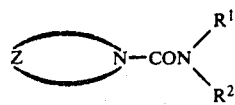

wherein:
$R^1$ and $R^2$ each represent a substituted or unsubstituted alicyclic, aliphatic, aromatic or heterocyclic moiety, or may be taken together with the nitrogen to which they are attached to form a heterocyclic ring; and
Z represents the atoms necessary to complete an azole ring containing at least two nitrogen atoms.

30. The dye image-receiving element of claim 29 wherein said azole ring is a benzotriazole, triazole, tetrazole, imidazole or benzimidazole.

31. The dye image-receiving element of claim 29 wherein said azole ring is a benzotriazole.

32. The dye image-receiving element of claim 29 wherein said compound has either of the following formulas:

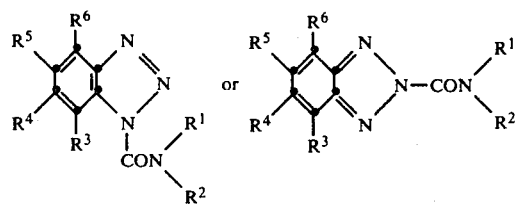

wherein:
$R^1$ and $R^2$ each represent a substituted or unsubstituted alicyclic, aliphatic, aromatic or heterocyclic moiety, or may be taken together with the nitrogen to which they are attached to form a heterocyclic ring; and
$R^3$, $R^4$, $R^5$ and $R^6$ each represent hydrogen, nitro, lower alkyl, halogen, carbamoyl, sulfamoyl, RCONH— or $RSO_2NH$—, wherein R is lower alkyl or aryl.

33. In a cover sheet comprising a transparent support having thereon, in sequence, a neutralizing layer and a timing layer, the improvement wherein said cover sheet contains a development restrainer azole compound having an alkali-hydrolyzable, N,N-disubstituted carbamoyl group, said compound having the following formula:

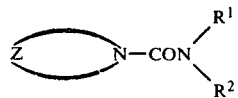

wherein:
$R^1$ and $R^2$ each represent a substituted or unsubstituted alicyclic, aliphatic, aromatic or heterocyclic moiety, or may be taken together with the nitrogen to which they are attached to form a heterocyclic ring; and
Z represents the atoms necessary to complete an azole ring containing at least two nitrogen atoms.